US 12,184,158 B2

United States Patent
Haag

(10) Patent No.: US 12,184,158 B2
(45) Date of Patent: Dec. 31, 2024

(54) METHOD AND LOAD CALCULATOR FOR PROVIDING TEMPERATURE INFORMATION FOR A HIGH VOLTAGE GENERATOR OF A MEDICAL IMAGING DEVICE

(71) Applicant: Siemens Healthcare GmbH, Erlangen (DE)

(72) Inventor: Nicole Haag, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 42 days.

(21) Appl. No.: 17/851,265

(22) Filed: Jun. 28, 2022

(65) Prior Publication Data

US 2023/0006513 A1 Jan. 5, 2023

(30) Foreign Application Priority Data

Jun. 30, 2021 (DE) .................. 10 2021 206 869.3

(51) Int. Cl.
*H02K 9/19* (2006.01)
*H02K 11/38* (2016.01)
*H05G 1/30* (2006.01)

(52) U.S. Cl.
CPC .............. *H02K 9/19* (2013.01); *H02K 11/38* (2016.01); *H05G 1/30* (2013.01)

(58) Field of Classification Search
CPC . H05G 1/30; H02K 11/38; H02K 9/19; H02K 9/193; H02K 9/197
See application file for complete search history.

(56) References Cited

U.S. PATENT DOCUMENTS

| 2005/0117698 A1 | 6/2005 | Lacey et al. |
| 2007/0058783 A1 | 3/2007 | Ebersberger |
| 2010/0111134 A1 | 5/2010 | Matsumoto |
| 2018/0352640 A1* | 12/2018 | Ono ............ A61B 6/563 |

(Continued)

FOREIGN PATENT DOCUMENTS

| CN | 101765290 A | 6/2010 |
| CN | 101896032 A | 11/2010 |

(Continued)

OTHER PUBLICATIONS

Han (CN 111024260 A) English Translation (Year: 2020).*

(Continued)

*Primary Examiner* — Tulsidas C Patel
*Assistant Examiner* — Robert E Mates
(74) *Attorney, Agent, or Firm* — Harness, Dickey & Pierce, P.L.C.

(57) ABSTRACT

A method for providing temperature information that relates to an inverter assembly having an inverter and a cooling body, comprises: receiving power loss data that relates to the inverter; receiving a set of thermodynamic coefficients that relates to a heating of the inverter, which is caused by power loss, a conduction of heat from the inverter to the cooling body and a transfer of heat from the cooling body to a cooling fluid; receiving cooling fluid temperature data that relates to the cooling fluid; calculating the temperature information based on the power loss data, the set of thermodynamic coefficients and the cooling fluid temperature data; and providing the temperature information.

16 Claims, 4 Drawing Sheets

(56) References Cited

U.S. PATENT DOCUMENTS

2020/0121274 A1 4/2020 Hofmann
2021/0307715 A1 10/2021 Krauss

FOREIGN PATENT DOCUMENTS

| CN | 111024260 A | * | 4/2020 | ............ G01K 13/00 |
|----|-------------|---|--------|---------|
| DE | 102006037971 B3 | | 11/2007 | |
| DE | 102005042088 B4 | | 3/2008 | |
| DE | 202018002830 U1 | | 10/2018 | |
| JP | 01255200 A | * | 10/1989 | |
| JP | 2004159419 A | * | 6/2004 | |
| JP | 2004220955 A | * | 8/2004 | |

OTHER PUBLICATIONS

Domoto (JP 2004220955 A) English Translation (Year: 2004).*
Asai (JP 01255200 A) English Translation (Year: 1989).*
Domoto (JP 2004159419 A) English Translation (Year: 2004).*
Gabriel Nagy, Ordinary Differential Equations, Jan. 18, 2021, Michigan State University (231-275) (Year: 2021).*
German Decision to Grant and English translation thereof dated Jun. 2, 2022.
German Office Action and English translation thereof dated Feb. 25, 2022.

* cited by examiner

METHOD AND LOAD CALCULATOR FOR PROVIDING TEMPERATURE INFORMATION FOR A HIGH VOLTAGE GENERATOR OF A MEDICAL IMAGING DEVICE

CROSS-REFERENCE TO RELATED APPLICATION(S)

The present application claims priority under 35 U.S.C. § 119 to German Patent Application No. DE 10 2021 206 869.3, filed Jun. 30, 2021, the entire contents of which are incorporated herein by reference.

FIELD

Embodiments of the present invention relate to a method for providing temperature information. Embodiments of the present invention moreover relate to a load calculator, a medical imaging device, a computer program product and a computer-readable storage medium.

BACKGROUND

On account of power loss, a build-up of heat occurs in the high voltage generator of the medical imaging device that has an X-ray tube. This build-up of heat is dependent upon the scan parameters, for example upon the tube voltage, the tube current and the scan duration and upon the connection to the cooling system of the gantry of the medical imaging device. In the event of overheating, in general a shutdown is provided for safety reasons. Although this can prevent damage to the high voltage generator, it can however also result in a possible problematic cancelation of the scan.

SUMMARY

Embodiments of the present invention provide an alternative to a conventional overheating protection for a high voltage generator of a medical imaging device.

Embodiments of the present invention relate to a method for providing temperature information that relates to an inverter assembly of a high voltage generator for an X-ray tube of a medical imaging device, wherein the inverter assembly has an inverter and a cooling body, the method comprising:
  receiving power loss data that relates to the inverter,
    receiving a set of thermodynamic coefficients that relates to a heating of the inverter, which is caused by power loss, a conduction of heat from the inverter to the cooling body and a transfer of heat from the cooling body to a cooling fluid, receiving cooling fluid temperature data that relates to the cooling fluid,
  calculating the temperature information based on the power loss data, the set of thermodynamic coefficients and the cooling fluid temperature data,
  providing the temperature information.

The temperature information can comprise for example a temporal temperature curve, in particular in the form of a curve, a temperature maximum, in particular in the form of a value, or a comparison result with respect to a temperature threshold value, in particular in the form of binary information. The temperature information can relate in particular to one or multiple components of the inverter assembly.

The temperature information can be calculated in particular sufficiently precisely in order to render it possible to protect against an overheating of the high voltage generator.

It is therefore possible in a cost-effective manner to extend the serviceable life of the components of the high voltage generator.

The thermodynamic coefficients of the set of thermodynamic coefficients can be in particular independent of temperature, in particular can be constant.

The cooling fluid temperature data can have for example a temperature value for the temperature of the cooling fluid. In particular, the cooling fluid temperature data can be provided from a constant temperature value for the temperature of the cooling fluid.

In accordance with one embodiment, the method moreover comprises:
  receiving tube current data that relates to a tube current for the X-ray tube,
  receiving tube voltage data that relates to a tube voltage for the X-ray tube,
  receiving intermediate circuit direct current voltage data that relates to an intermediate circuit direct current voltage of the inverter,
  wherein the power loss data is calculated based on the tube current data, the tube voltage data and the intermediate circuit direct current data.

In the inverter, in particular in the semiconductor junctions of the inverter, heat is produced on account of power loss. It can be assumed that the power loss is transferred to a housing of the inverter directly, in particular without time lag.

The power loss is dependent upon operating parameters of the high voltage generator. The operating parameters can comprise in particular the tube current, the tube voltage and the intermediate circuit direct current voltage.

In particular, it is possible to provide that the power loss data is calculated by applying linear interpolation to tabulated values of the operating parameters and corresponding power loss values.

In particular, it can be provided that the power loss data is calculated directly by applying a provided power loss formula to the values of the operating parameters.

It is possible in the tube current data to take into consideration in particular a time-dependent tube current, for example in the form of a temporal tube current curve. It is possible in the tube voltage data to take into consideration in particular a time-dependency of the tube voltage, for example in the form of a temporal tube voltage curve. It is possible in the intermediate circuit direct current voltage data to take into consideration in particular a time dependency of the intermediate circuit direct current voltage data, for example in the form of a temporal intermediate circuit direct current voltage curve.

In particular, it is possible to understand receiving a constant value for the tube current in conjunction with receiving a constant value for a scan duration as receiving a temporal tube current curve because at the end of the scan duration the tube current changes. The same applies for the tube voltage and/or the intermediate circuit direct current voltage.

The temporal tube current curve can be calculated for example based on a tube power profile and/or an investigation protocol. The temporal tube voltage curve can be calculated for example based on a tube power profile and/or an investigation protocol. The temporal intermediate circuit direct current voltage curve can be calculated for example based on a tube power profile and/or an investigation protocol.

In particular, it can be provided that the intermediate circuit direct current voltage is primarily dependent upon a mains input voltage to a mains input circuit of the high voltage generator and/or that the intermediate circuit direct current voltage is essentially constant and/or is essentially protected from an overvoltage.

In particular, a temperature dependency of the power loss can be taken into consideration or ignored in the power loss data.

One embodiment provides that the set of thermodynamic coefficients is based on simulations and/or measurements.

For example, the set of thermodynamic coefficients can be calculated based on an adaptation, in particular in the form of fits, of a thermodynamic model that relates to the heating of the inverter, which is caused by power loss, the conduction of heat from the inverter to the cooling body and the heat transfer from the cooling body to the cooling fluid, to the simulations and/or the measurements. It is possible for the simulations and/or the measurements to be provided for example by a manufacturer of the high voltage generator and/or to be performed during a system integration.

One embodiment provides that the inverter has a first half bridge and a second half bridge that can differ from one another in particular with respect to the power loss, wherein the power loss data comprises first power loss data that relates to the first half bridge and second power loss data that relates to the second half bridge, wherein the set of thermodynamic coefficients comprises a coefficient that relates to a heating of the first half bridge that is based on a power loss, wherein the set of thermodynamic coefficients comprises a coefficient that relates to a heating of the second half bridge that is based on a power loss.

One embodiment provides that the calculation of the temperature information is based on a thermodynamic model of the cooling body, accordingly the cooling body has a first region and a second region, wherein the set of thermodynamic coefficients relates to a conduction of heat from the inverter to the cooling body and a transfer of heat from the cooling body to a cooling fluid in that the set of thermodynamic coefficients relates to a conduction of heat from the inverter to the first region of the cooling body, a conduction of heat from the first region of the cooling body to the second region of the cooling body and to a transfer of heat from the second region of the cooling body to a cooling fluid.

In this manner, it is possible to better represent the different time constants of the temperature curve. The temperature of the first region of the cooling body can be understood for example as an intermediary cooling body temperature. The temperature of the second region of the cooling body can be understood for example as an actually measurable temperature of the cooling body. In this manner, it is possible to take into consideration temperature inhomogeneities. It is also possible to divide the cooling body in the thermodynamic model into more than two regions.

One embodiment provides that the calculation of the temperature information comprises solving a differential equation system, wherein the differential equation system comprises multiple coupled inhomogeneous linear ordinary differential equations of the first order having constant coefficients.

One example for such a differential equation system states:

$$\dot{T}_{N1} = k_{i1} \cdot P_{loss,1} - k_{i2} \cdot (T_{N1} - T_{HSi})$$

$$\dot{T}_{N2} = k_{i3} \cdot P_{loss,2} - k_{i4} \cdot (T_{N2} - T_{HSi})$$

$$\dot{T}_{HSi} = k_{i5} \cdot (T_{N1} - T_{HSi}) + k_{i6} \cdot (T_{N2} - T_{HSi}) - k_{i7} \cdot (T_{HSi} - T_{HS})$$

$$\dot{T}_{HS} = k_{i8} \cdot (T_{HSi} - T_{HS}) - k_{i9} \cdot (T_{HS} - T_K)$$

$P_{loss,1}$ is the power loss of the first half bridge and the temperature of said first half bridge is $T_{N1}$. $P_{loss,2}$ is the power loss of the second half bridge and the temperature of said second half bridge is $T_{N2}$. $T_{HSi}$ is the temperature of the first region of the cooling body. $T_{HS}$ is the temperature of the second region of the cooling body. $T_K$ is the temperature of the cooling fluid. $k_{i1} \ldots k_{i9}$ form the set of thermodynamic coefficients.

One embodiment provides that a coefficient matrix for a matrix representation of the differential equation system is determined based on the set of thermodynamic coefficients, wherein an inhomogeneities vector for a matrix representation of the differential equation system is determined based on the set of thermodynamic coefficients, the power loss data and the cooling fluid temperature, wherein the differential equation system is solved based on a matrix operation.

One example for such a matrix representation states:

$$\begin{pmatrix} \dot{T}_{N1} \\ \dot{T}_{N2} \\ \dot{T}_{HSi} \\ \dot{T}_{HS} \end{pmatrix} = \begin{pmatrix} -k_{i2} & 0 & k_{i2} & 0 \\ 0 & -k_{i4} & k_{i4} & 0 \\ k_{i5} & k_{i6} & -k_{i5}-k_{i6}-k_{i7} & k_{i7} \\ 0 & 0 & k_{i8} & -k_{i8}-k_{i9} \end{pmatrix} \cdot \begin{pmatrix} T_{N1} \\ T_{N2} \\ T_{HSi} \\ T_{HS} \end{pmatrix} + \begin{pmatrix} k_{i1} \cdot P_{loss,1} \\ k_{i3} \cdot P_{loss,2} \\ 0 \\ k_{i9} \cdot T_k \end{pmatrix}$$

In summary, this matrix representation can also be formulated as follows:

$$\vec{\dot{T}} = ((M_{Gen})) \cdot \vec{T} + \vec{V}$$

$\vec{T}$ is the vector of the temperatures. $\vec{V}$ is the vector of the inhomogeneities, in other words the heat sources and heat sinks. $M_{Gen}$ is the coefficient matrix.

The differential equation system can be solved for example based on matrix multiplications. The matrix operation can comprise in particular a matrix potential with respect to the coefficient matrix.

Alternatively or in addition to a matrix-based solution of the differential equation system, it is possible to use methods for temperature simulation, for example as FEM simulation, and/or for iterative integration, in particular if a sufficiently high computing power is provided in order to keep the computing time as short as possible.

One embodiment provides that the set of thermodynamic coefficients comprises a coefficient that relates to a dependency of a temperature difference, which occurs between a semiconductor junction of the inverter and a housing of the inverter and said housing surrounds the semiconductor junction, upon a power loss of the semiconductor junction of the inverter, wherein the temperature information relates to a temperature at the semiconductor junction of the inverter.

The maximum temperature TJ at a housing of the inverter can be calculated for example as follows:

$$T_J = \max(k_{JN} \cdot P_{loss,1} + T_{N1}, k_{JN} \cdot P_{loss,2} + T_{N2})$$

In this case, $K_{JN}$ is the coefficient that relates to a dependency of a temperature difference, which occurs between a semiconductor junction of the inverter and a housing of the inverter and said housing surrounds the semiconductor junction, upon a power loss of the semiconductor junction of the inverter.

One embodiment provides that the calculation of the temperature information comprises a temporal localization of a temperature maximum, wherein a calculation of a temporal temperature curve is adapted in dependence upon a temporal localization of the temperature maximum, wherein the temperature information is calculated based on the temporal temperature curve.

In this manner, it is possible to take into consideration a heating of components of the inverter that is delayed with respect to the end time point of the scan. This can occur in particular in dependence upon whether a temperature threshold value is exceeded at the end time point of the scan. The temperature maximum can be localized for example based on parabolic interpolation.

One embodiment provides that threshold value data is received, wherein the temperature information is moreover calculated based on the threshold value data and at least one threshold value comparison.

In addition, it is possible to monitor the average scan power in different time windows.

One embodiment provides that time information, which relates to a cooling pause for the high voltage generator, is calculated based on the temperature information, wherein the time information is provided. The cooling pause for the high voltage generator can be designed in particular so as to avoid an overheating of the high voltage generator during the medical imaging investigation. The time information can comprise for example a time interval, in particular in the form of a countdown to the earliest possible start time point of the scan, and/or a time that indicates the earliest possible start time point of the scan.

One embodiment provides that parameter change information that relates to a parameter change for a medical imaging investigation via the medical imaging device is calculated based on the temperature information, wherein the parameter change information is provided.

The parameter change for a medical imaging investigation can be designed in particular so as to avoid an overheating of the high voltage generator during the medical imaging investigation. Parameter change information can comprise for example a parameter value change relative to an original parameter value and/or can comprise a changed parameter value. The parameter change can relate to in particular the tube current, the tube voltage, the intermediate circuit direct current voltage and/or to the scan duration. The parameter change information can comprise in particular a recommendation with respect to a selection and/or a change of an investigation protocol for the medical imaging investigation.

The parameter change can then be used in particular if it is not possible to prevent an overheating only with the aid of a cooling pause.

Embodiments of the present invention moreover relate to a load calculator for providing temperature information that relates to an inverter assembly of a high voltage generator for an X-ray tube of a medical imaging device, wherein the inverter assembly has an inverter and a cooling body, the load calculator having:

a power loss data receiving unit for receiving power loss data that relates to the inverter, a coefficient receiving unit for receiving a set of thermodynamic coefficients that relates to a heating of the inverter, which is caused by power loss, a conduction of heat from the inverter to the cooling body and a transfer of heat from the cooling body to a cooling fluid, a cooling fluid temperature data receiving unit for receiving cooling fluid temperature data that relates to the cooling fluid, a computing unit for calculating the temperature information based on the power loss data, the set of thermodynamic coefficients and the cooling fluid temperature data, a providing unit for providing the temperature information.

Embodiments of the present invention moreover relate to a medical imaging device having an X-ray tube and a load calculator in accordance with the embodiments of the present invention.

One embodiment provides that the medical imaging device is an X-ray device, a C-arm X-ray device or a computer tomography device.

The described method renders it possible to sufficiently rapidly calculate and provide the temperature information, for example in order to be able to display scan approvals or required waiting times on a user interface without significant time lag.

The high voltage generator can be designed, in particular specified, for example for relatively low powers, in particular for powers up to 90 kW. It is possible to use more cost-effective components that are less robust with respect to heat since owing to the precise projection (simulation) of the temperature curves the heat resistance that is provided can be used up completely.

The method for providing temperature information can be in particular a computer-implemented method.

Embodiments of the present invention moreover relate to a computer program product having a computer program, which can be loaded directly into a storage unit of a data processing system, having program sections in order to implement all the steps of a method in accordance with embodiments of the present invention if the program sections are executed by the data processing system.

The computer program product can be for example the computer program or can comprise at least one additional component in addition to the computer program. The at least one additional component of the computer program product can be provided as hardware and/or as software.

The computer program product can have for example a storage medium, on which at least a part of the computer program product is stored, and/or a key for the authentication of a user of the computer program product, in particular in the form of a dongle. The computer program product and/or the computer program can have for example a cloud application program that is designed so as to distribute program sections of the computer program to various processing units, in particular various computers, of a cloud computing system, wherein each of the processing units is designed so as to execute one or multiple program sections of the computer program.

Embodiments of the present invention moreover relate to a computer-readable storage medium and program sections that can be read and executed by a data processing system are stored on said computer-readable storage medium in order to implement all the steps of a method in accordance with embodiments of the present invention if the program sections are executed by the data processing system.

It is possible on the computer-readable storage medium to store for example the computer program product according to one of the embodiments that are disclosed in this application and/or the computer program according to one of the embodiments that are disclosed in this application. The computer-readable storage medium can be for example a memory stick, a hard disk or another data carrier that can be in particular detachably connected to the data processing system or can be fixedly integrated into the data processing system. The computer-readable storage medium can form for example a region of the storage system of the data processing system.

The data processing system can have for example one or multiple components in the form of hardware and/or one or multiple components in the form of software. The data processing system can be formed for example at least in part by a cloud computing system. The data processing system can be and/or can have for example a cloud computing system, a computer network, a computer, a tablet computer, a smartphone or similar or a combination thereof.

The hardware can cooperate for example with software and/or can be configured via software. The software can be executed for example via the hardware. The hardware can be for example a storage system, an FPGA system (field programmable gate array), an ASIC system (application specific integrated circuit), a microcontroller system, a processor system and combinations thereof. The processor system can have for example a microprocessor and/or multiple cooperating microprocessors.

The steps of the method can be executed for example in a processor, in particular in the form of calculations.

A data transfer between components of the data processing system can be performed for example in each case via a suitable data transfer interface. The data transfer interface for transferring data to and/or from a component of a data processing system can be realized at least in part in the form of software and/or at least in part in the form of hardware. The data transfer interface can be designed for example so as to store data in and/or so as to read data from a region of the storage system, wherein one or multiple components of the data processing system can be accessed on this region of the storage system.

Data, in particular the power loss data, the set of thermodynamic coefficients and/or the cooling fluid temperature data can be received for example in that a signal that carries the data is received and/or in that the data is read and in particular is read from a computer-readable storage medium. Data, in particular the temperature information and/or the time information can be provided for example in that a signal that carries the data is transmitted and/or in that the data is written into a computer-readable storage medium and/or in that the data is displayed on a screen.

In particular, the power loss data can be calculated based on the tube current data, the tube voltage data and the intermediate direct current voltage data and said power loss data can be subsequently cached in a cache of the data processing system, in particular the load calculator, from where said power loss data can be received by the power loss data receiving unit.

Within the scope of the present invention, it is possible to combine features that are described with respect to different embodiments of the present invention and/or different claim categories (method, use, apparatus, system, arrangement etc.) to form further embodiments of the present invention. For example, a claim that relates to an apparatus can also be further developed with features that are described or claimed in connection with a method and vice versa. Functional features of a method can be provided in this case by accordingly provided objective components. In addition to the embodiments of the present invention that are explicitly described in this application, diverse further embodiments of the present invention are also conceivable, which the person skilled in the art can arrive at without departing the scope of the present invention that is provided by the claims.

BRIEF DESCRIPTION OF THE DRAWINGS

The present invention is explained below with the aid of exemplary embodiments with reference to the attached figures. The illustration in the figures is schematic, heavily simplified and not necessarily true to scale.

DETAILED DESCRIPTION

Figure 1:
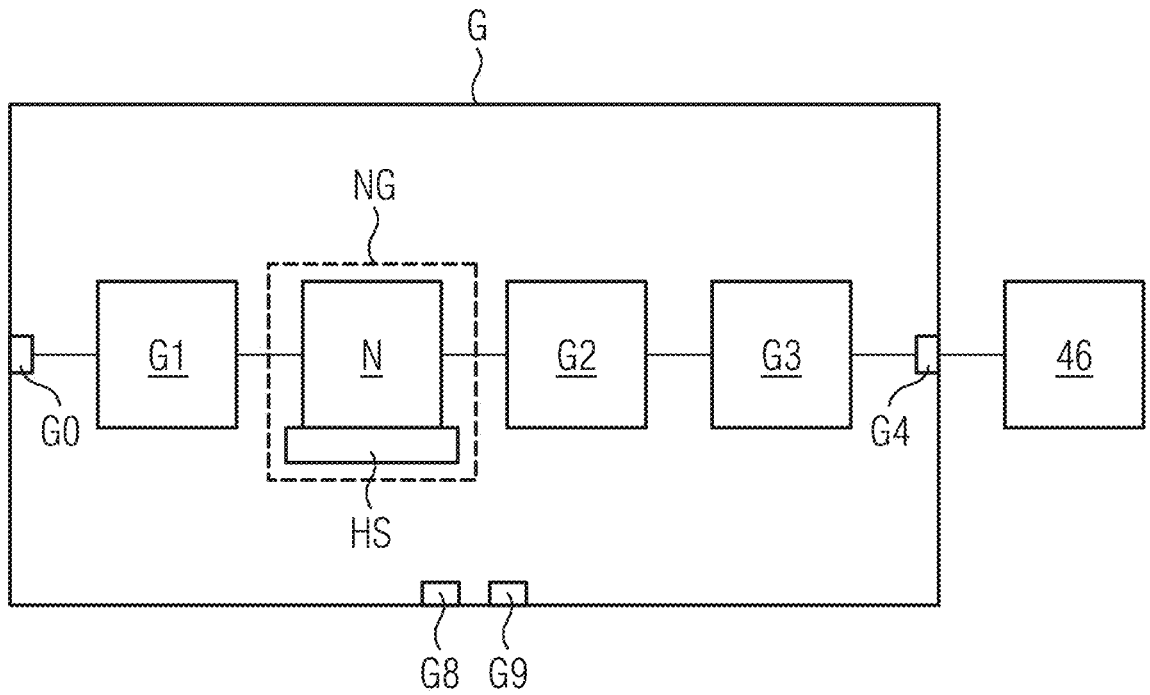
FIG. 1 shows a schematic illustration of a high voltage generator and an X-ray tube.

Embodiments of the present invention provide an alternative to a conventional overheating protection for a high voltage generator of a medical imaging device.

Embodiments of the present invention relate to a method for providing temperature information that relates to an inverter assembly of a high voltage generator for an X-ray tube of a medical imaging device, wherein the inverter assembly has an inverter and a cooling body, the method comprising:
    receiving power loss data that relates to the inverter, receiving a set of thermodynamic coefficients that relates to a heating of the inverter, which is caused by power loss, a conduction of heat from the inverter to the cooling body and a transfer of heat from the cooling body to a cooling fluid, receiving cooling fluid temperature data that relates to the cooling fluid,
    calculating the temperature information based on the power loss data, the set of thermodynamic coefficients and the cooling fluid temperature data, providing the temperature information.

The temperature information can comprise for example a temporal temperature curve, in particular in the form of a curve, a temperature maximum, in particular in the form of a value, or a comparison result with respect to a temperature threshold value, in particular in the form of binary information. The temperature information can relate in particular to one or multiple components of the inverter assembly.

The temperature information can be calculated in particular sufficiently precisely in order to render it possible to protect against an overheating of the high voltage generator. It is therefore possible in a cost-effective manner to extend the serviceable life of the components of the high voltage generator.

The thermodynamic coefficients of the set of thermodynamic coefficients can be in particular independent of temperature, in particular can be constant.

The cooling fluid temperature data can have for example a temperature value for the temperature of the cooling fluid. In particular, the cooling fluid temperature data can be provided from a constant temperature value for the temperature of the cooling fluid.

In accordance with one embodiment, the method moreover comprises:
    receiving tube current data that relates to a tube current for the X-ray tube, receiving tube voltage data that relates to a tube voltage for the X-ray tube, receiving intermediate circuit direct current voltage data that relates to an intermediate circuit direct current voltage of the inverter, wherein the power loss data is calculated based on the tube current data, the tube voltage data and the intermediate circuit direct current data.

In the inverter, in particular in the semiconductor junctions of the inverter, heat is produced on account of power loss. It can be assumed that the power loss is transferred to a housing of the inverter directly, in particular without time lag.

The power loss is dependent upon operating parameters of the high voltage generator. The operating parameters can comprise in particular the tube current, the tube voltage and the intermediate circuit direct current voltage.

In particular, it is possible to provide that the power loss data is calculated by applying linear interpolation to tabulated values of the operating parameters and corresponding power loss values.

In particular, it can be provided that the power loss data is calculated directly by applying a provided power loss formula to the values of the operating parameters.

It is possible in the tube current data to take into consideration in particular a time-dependent tube current, for example in the form of a temporal tube current curve. It is possible in the tube voltage data to take into consideration in particular a time-dependency of the tube voltage, for example in the form of a temporal tube voltage curve. It is possible in the intermediate circuit direct current voltage data to take into consideration in particular a time dependency of the intermediate circuit direct current voltage data, for example in the form of a temporal intermediate circuit direct current voltage curve.

In particular, it is possible to understand receiving a constant value for the tube current in conjunction with receiving a constant value for a scan duration as receiving a temporal tube current curve because at the end of the scan duration the tube current changes. The same applies for the tube voltage and/or the intermediate circuit direct current voltage.

The temporal tube current curve can be calculated for example based on a tube power profile and/or an investigation protocol. The temporal tube voltage curve can be calculated for example based on a tube power profile and/or an investigation protocol. The temporal intermediate circuit direct current voltage curve can be calculated for example based on a tube power profile and/or an investigation protocol.

In particular, it can be provided that the intermediate circuit direct current voltage is primarily dependent upon a mains input voltage to a mains input circuit of the high voltage generator and/or that the intermediate circuit direct current voltage is essentially constant and/or is essentially protected from an overvoltage.

In particular, a temperature dependency of the power loss can be taken into consideration or ignored in the power loss data.

One embodiment provides that the set of thermodynamic coefficients is based on simulations and/or measurements.

For example, the set of thermodynamic coefficients can be calculated based on an adaptation, in particular in the form of fits, of a thermodynamic model that relates to the heating of the inverter, which is caused by power loss, the conduction of heat from the inverter to the cooling body and the heat transfer from the cooling body to the cooling fluid, to the simulations and/or the measurements. It is possible for the simulations and/or the measurements to be provided for example by a manufacturer of the high voltage generator and/or to be performed during a system integration.

One embodiment provides that the inverter has a first half bridge and a second half bridge that can differ from one another in particular with respect to the power loss, wherein the power loss data comprises first power loss data that relates to the first half bridge and second power loss data that relates to the second half bridge, wherein the set of thermodynamic coefficients comprises a coefficient that relates to a heating of the first half bridge that is based on a power loss, wherein the set of thermodynamic coefficients comprises a coefficient that relates to a heating of the second half bridge that is based on a power loss.

One embodiment provides that the calculation of the temperature information is based on a thermodynamic model of the cooling body, accordingly the cooling body has a first region and a second region, wherein the set of thermodynamic coefficients relates to a conduction of heat from the inverter to the cooling body and a transfer of heat from the cooling body to a cooling fluid in that the set of thermodynamic coefficients relates to a conduction of heat from the inverter to the first region of the cooling body, a conduction of heat from the first region of the cooling body to the second region of the cooling body and to a transfer of heat from the second region of the cooling body to a cooling fluid.

In this manner, it is possible to better represent the different time constants of the temperature curve. The temperature of the first region of the cooling body can be understood for example as an intermediary cooling body temperature. The temperature of the second region of the cooling body can be understood for example as an actually measurable temperature of the cooling body. In this manner, it is possible to take into consideration temperature inhomogeneities. It is also possible to divide the cooling body in the thermodynamic model into more than two regions.

One embodiment provides that the calculation of the temperature information comprises solving a differential equation system, wherein the differential equation system comprises multiple coupled inhomogeneous linear ordinary differential equations of the first order having constant coefficients.

One example for such a differential equation system states:

$$\dot{T}_{N1} = k_{i1} \cdot P_{loss,1} - k_{i2} \cdot (T_{N1} - T_{HSi})$$

$$\dot{T}_{N2} = k_{i3} \cdot P_{loss,2} - k_{i4} \cdot (T_{N2} - T_{HSi})$$

$$\dot{T}_{HSi} = k_{i5} \cdot (T_{N1} - T_{HSi}) + k_{i6} \cdot (T_{N2} - T_{HSi}) - k_{i7} \cdot (T_{HSi} - T_{HS})$$

$$\dot{T}_{HS} = k_{i8} \cdot (T_{HSi} - T_{HS}) - k_{i9} \cdot (T_{HS} - T_K)$$

$P_{loss,1}$ is the power loss of the first half bridge and the temperature of said first half bridge is $T_{N1}$. $P_{loss,2}$ is the power loss of the second half bridge and the temperature of said second half bridge is $T_{N2}$. $T_{HSi}$ is the temperature of the first region of the cooling body. $T_{HS}$ is the temperature of the second region of the cooling body. $T_K$ is the temperature of the cooling fluid. $k_{i1} \ldots k_{i9}$ form the set of thermodynamic coefficients.

One embodiment provides that a coefficient matrix for a matrix representation of the differential equation system is determined based on the set of thermodynamic coefficients, wherein an inhomogeneities vector for a matrix representation of the differential equation system is determined based on the set of thermodynamic coefficients, the power loss data and the cooling fluid temperature, wherein the differential equation system is solved based on a matrix operation.

One example for such a matrix representation states:

$$\begin{pmatrix} \dot{T}_{N1} \\ \dot{T}_{N2} \\ \dot{T}_{HSi} \\ \dot{T}_{HS} \end{pmatrix} = \begin{pmatrix} -k_{i2} & 0 & k_{i2} & 0 \\ 0 & -k_{i4} & k_{i4} & 0 \\ k_{i5} & k_{i6} & -k_{i5}-k_{i6}-k_{i7} & k_{i7} \\ 0 & 0 & k_{i8} & -k_{i8}-k_{i9} \end{pmatrix} \cdot \begin{pmatrix} T_{N1} \\ T_{N2} \\ T_{HSi} \\ T_{HS} \end{pmatrix} + \begin{pmatrix} k_{i1} \cdot P_{loss,1} \\ k_{i3} \cdot P_{loss,2} \\ 0 \\ k_{i9} \cdot T_k \end{pmatrix}$$

In summary, this matrix representation can also be formulated as follows:

$$\dot{\vec{T}} = ((M_{Gen})) \cdot \vec{T} + \vec{V}$$

$\dot{T}$ is the vector of the temperatures. $\dot{V}$ is the vector of the inhomogeneities, in other words the heat sources and heat sinks. $M_{Gen}$ is the coefficient matrix.

The differential equation system can be solved for example based on matrix multiplications. The matrix operation can comprise in particular a matrix potential with respect to the coefficient matrix.

Alternatively or in addition to a matrix-based solution of the differential equation system, it is possible to use methods for temperature simulation, for example as FEM simulation, and/or for iterative integration, in particular if a sufficiently high computing power is provided in order to keep the computing time as short as possible.

One embodiment provides that the set of thermodynamic coefficients comprises a coefficient that relates to a dependency of a temperature difference, which occurs between a semiconductor junction of the inverter and a housing of the inverter and said housing surrounds the semiconductor junction, upon a power loss of the semiconductor junction of the inverter, wherein the temperature information relates to a temperature at the semiconductor junction of the inverter.

The maximum temperature TJ at a housing of the inverter can be calculated for example as follows:

$$T_J = \max(k_{JN} \cdot P_{loss,1} + T_{N1}, k_{JN} \cdot P_{loss,2} + T_{N2})$$

In this case, $K_{JN}$ is the coefficient that relates to a dependency of a temperature difference, which occurs between a semiconductor junction of the inverter and a housing of the inverter and said housing surrounds the semiconductor junction, upon a power loss of the semiconductor junction of the inverter.

One embodiment provides that the calculation of the temperature information comprises a temporal localization of a temperature maximum, wherein a calculation of a temporal temperature curve is adapted in dependence upon a temporal localization of the temperature maximum, wherein the temperature information is calculated based on the temporal temperature curve.

In this manner, it is possible to take into consideration a heating of components of the inverter that is delayed with respect to the end time point of the scan. This can occur in particular in dependence upon whether a temperature threshold value is exceeded at the end time point of the scan. The temperature maximum can be localized for example based on parabolic interpolation.

One embodiment provides that threshold value data is received, wherein the temperature information is moreover calculated based on the threshold value data and at least one threshold value comparison.

In addition, it is possible to monitor the average scan power in different time windows.

One embodiment provides that time information, which relates to a cooling pause for the high voltage generator, is calculated based on the temperature information, wherein the time information is provided. The cooling pause for the high voltage generator can be designed in particular so as to avoid an overheating of the high voltage generator during the medical imaging investigation. The time information can comprise for example a time interval, in particular in the form of a countdown to the earliest possible start time point of the scan, and/or a time that indicates the earliest possible start time point of the scan.

One embodiment provides that parameter change information that relates to a parameter change for a medical imaging investigation via the medical imaging device is calculated based on the temperature information, wherein the parameter change information is provided.

The parameter change for a medical imaging investigation can be designed in particular so as to avoid an overheating of the high voltage generator during the medical imaging investigation. Parameter change information can comprise for example a parameter value change relative to an original parameter value and/or can comprise a changed parameter value. The parameter change can relate to in particular the tube current, the tube voltage, the intermediate circuit direct current voltage and/or to the scan duration. The parameter change information can comprise in particular a recommendation with respect to a selection and/or a change of an investigation protocol for the medical imaging investigation.

The parameter change can then be used in particular if it is not possible to prevent an overheating only with the aid of a cooling pause.

Embodiments of the present invention moreover relate to a load calculator for providing temperature information that relates to an inverter assembly of a high voltage generator for an X-ray tube of a medical imaging device, wherein the inverter assembly has an inverter and a cooling body, the load calculator having:
- a power loss data receiving unit for receiving power loss data that relates to the inverter,
- a coefficient receiving unit for receiving a set of thermodynamic coefficients that relates to a heating of the inverter, which is caused by power loss, a conduction of heat from the inverter to the cooling body and a transfer of heat from the cooling body to a cooling fluid,
- a cooling fluid temperature data receiving unit for receiving cooling fluid temperature data that relates to the cooling fluid,
- a computing unit for calculating the temperature information based on the power loss data, the set of thermodynamic coefficients and the cooling fluid temperature data,
- a providing unit for providing the temperature information.

Embodiments of the present invention moreover relate to a medical imaging device having an X-ray tube and a load calculator in accordance with the embodiments of the present invention.

One embodiment provides that the medical imaging device is an X-ray device, a C-arm X-ray device or a computer tomography device.

The described method renders it possible to sufficiently rapidly calculate and provide the temperature information, for example in order to be able to display scan approvals or required waiting times on a user interface without significant time lag.

The high voltage generator can be designed, in particular specified, for example for relatively low powers, in particular for powers up to 90 kW. It is possible to use more cost-effective components that are less robust with respect to heat since owing to the precise projection (simulation) of the temperature curves the heat resistance that is provided can be used up completely.

The method for providing temperature information can be in particular a computer-implemented method.

Embodiments of the present invention moreover relate to a computer program product having a computer program, which can be loaded directly into a storage unit of a data processing system, having program sections in order to implement all the steps of a method in accordance with embodiments of the present invention if the program sections are executed by the data processing system.

The computer program product can be for example the computer program or can comprise at least one additional component in addition to the computer program. The at least one additional component of the computer program product can be provided as hardware and/or as software.

The computer program product can have for example a storage medium, on which at least a part of the computer program product is stored, and/or a key for the authentication of a user of the computer program product, in particular in the form of a dongle. The computer program product and/or the computer program can have for example a cloud application program that is designed so as to distribute program sections of the computer program to various processing units, in particular various computers, of a cloud computing system, wherein each of the processing units is designed so as to execute one or multiple program sections of the computer program.

Embodiments of the present invention moreover relate to a computer-readable storage medium and program sections that can be read and executed by a data processing system are stored on said computer-readable storage medium in order to implement all the steps of a method in accordance with embodiments of the present invention if the program sections are executed by the data processing system.

It is possible on the computer-readable storage medium to store for example the computer program product according to one of the embodiments that are disclosed in this application and/or the computer program according to one of the embodiments that are disclosed in this application. The computer-readable storage medium can be for example a memory stick, a hard disk or another data carrier that can be in particular detachably connected to the data processing system or can be fixedly integrated into the data processing system. The computer-readable storage medium can form for example a region of the storage system of the data processing system.

The data processing system can have for example one or multiple components in the form of hardware and/or one or multiple components in the form of software. The data processing system can be formed for example at least in part by a cloud computing system. The data processing system can be and/or can have for example a cloud computing system, a computer network, a computer, a tablet computer, a smartphone or similar or a combination thereof.

The hardware can cooperate for example with software and/or can be configured via software. The software can be executed for example via the hardware. The hardware can be for example a storage system, an FPGA system (field programmable gate array), an ASIC system (application specific integrated circuit), a microcontroller system, a processor system and combinations thereof. The processor system can have for example a microprocessor and/or multiple cooperating microprocessors.

The steps of the method can be executed for example in a processor, in particular in the form of calculations.

A data transfer between components of the data processing system can be performed for example in each case via a suitable data transfer interface. The data transfer interface for transferring data to and/or from a component of a data processing system can be realized at least in part in the form of software and/or at least in part in the form of hardware. The data transfer interface can be designed for example so as to store data in and/or so as to read data from a region of the storage system, wherein one or multiple components of the data processing system can be accessed on this region of the storage system.

Data, in particular the power loss data, the set of thermodynamic coefficients and/or the cooling fluid temperature data can be received for example in that a signal that carries the data is received and/or in that the data is read and in particular is read from a computer-readable storage medium. Data, in particular the temperature information and/or the time information can be provided for example in that a signal that carries the data is transmitted and/or in that the data is written into a computer-readable storage medium and/or in that the data is displayed on a screen.

In particular, the power loss data can be calculated based on the tube current data, the tube voltage data and the intermediate direct current voltage data and said power loss data can be subsequently cached in a cache of the data processing system, in particular the load calculator, from where said power loss data can be received by the power loss data receiving unit.

FIG. 1 shows a schematic illustration of a high voltage generator G and an X-ray tube 46.

The high voltage generator G has a mains connection G0, a mains input circuit G1, an inverter assembly NG, the transformer G2, the rectifier G3 and the high voltage connection G4 for the X-ray tube 46.

The high voltage generator G moreover has data transfer interfaces G8 and G9, for example for receiving control data and/or for transmitting operating data and/or measurement data.

Figure 2:
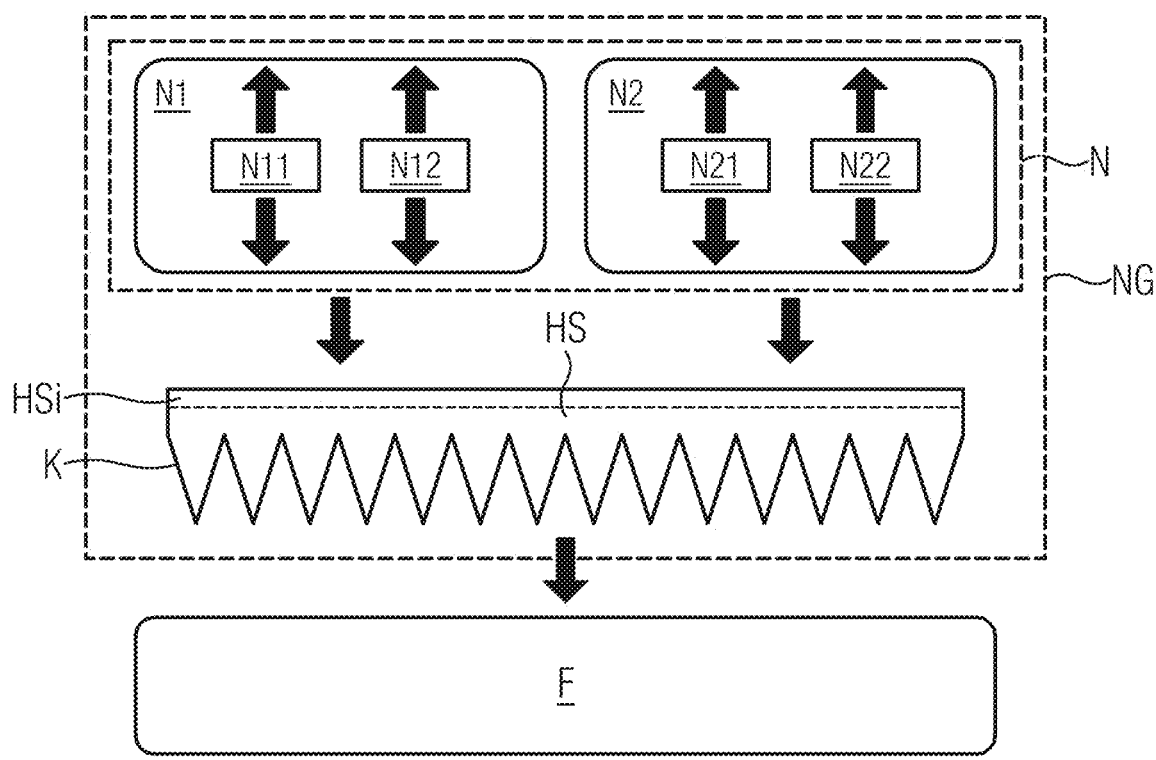
FIG. 2 shows a schematic illustration of an inverter assembly.

FIG. 2 illustrates a schematic illustration of an inverter assembly NG. The inverter assembly NG has an inverter N and a cooling body K. The inverter N has a first half bridge N1 and a second half bridge N2. The first half bridge N1 has a first semiconductor junction N11 and a second semiconductor junction N12. The second half bridge N2 has a first semiconductor junction N21 and a second semiconductor junction N22. The heat flow between the components of the inverter assembly NG is illustrated by the arrows. The cooling body K has a first region HSi and a second region HS, wherein heat from the first region HSi is transferred to the second region HS and transfers from the second region HS to the cooling fluid F. The cooling fluid F can be for example cooling air.

Figure 3:
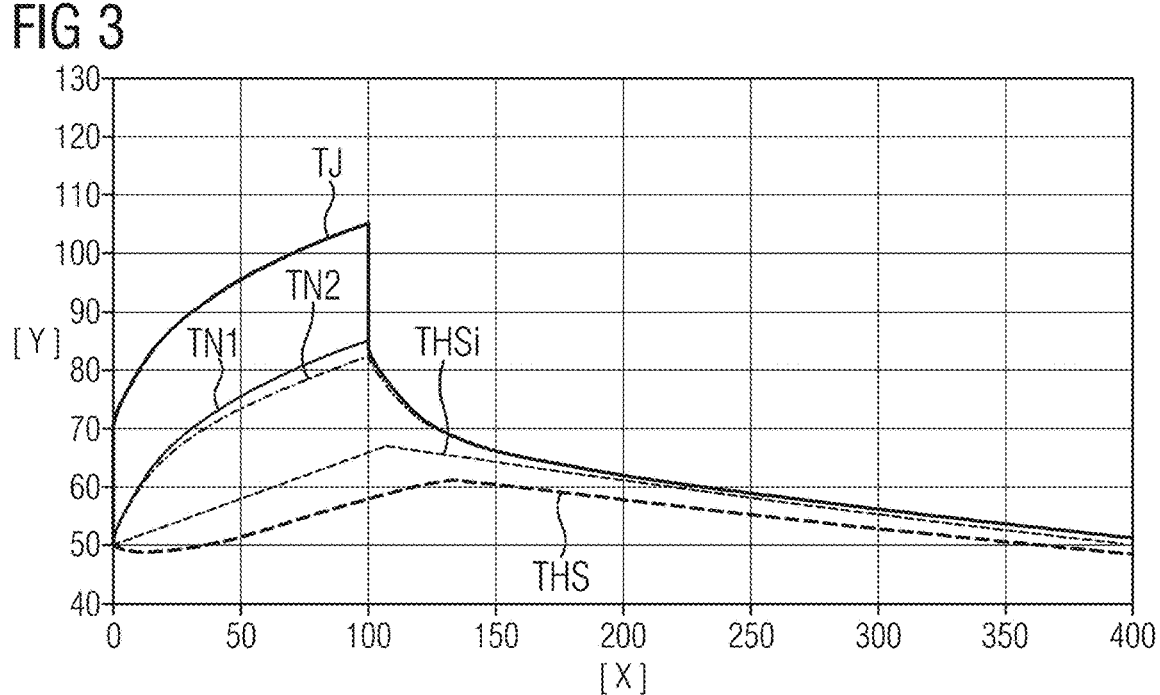
FIG. 3 shows a diagram having temperature curves that are calculated by the load calculator.

FIG. 3 shows a diagram having temperature curves that are calculated by the load calculator for various components or regions of the inverter assembly NG. The calculation was based on a tube voltage of 130 kV, a tube current of 150 mA, a scan duration of 100 seconds and an intermediate circuit direct current voltage of 712 V. The time in seconds is plotted on the X-axis. The temperature in ° C. is plotted on the Y-axis.

The calculation M4 of the temperature information TI is based on a thermodynamic model of the cooling body K, accordingly the cooling body K has a first region HSi and a second region HS, wherein the set of thermodynamic coefficients relates to a conduction of heat from the inverter N to the cooling body K and a transfer of heat from the cooling body K to a cooling fluid F in that the set of thermodynamic coefficients relates to a conduction of heat from the inverter N to the first region HSi of the cooling body K, a conduction of heat from the first region HSi of the cooling body K to the second region HS of the cooling body K and a transfer of heat from the second region HS of the cooling body K to a cooling fluid F.

THSi is the temperature curve of the first region HSi of the cooling body K. THS is the temperature curve of the second region HS of the cooling body K. TN1 is the temperature curve of the first half bridge N1. TN2 is the temperature curve of the second half bridge N2. TJ is the curve of the in each case highest temperature of the set of temperatures that is provided from the temperatures of the semiconductor junctions N11, N12, N21 and N22.

Figure 4:
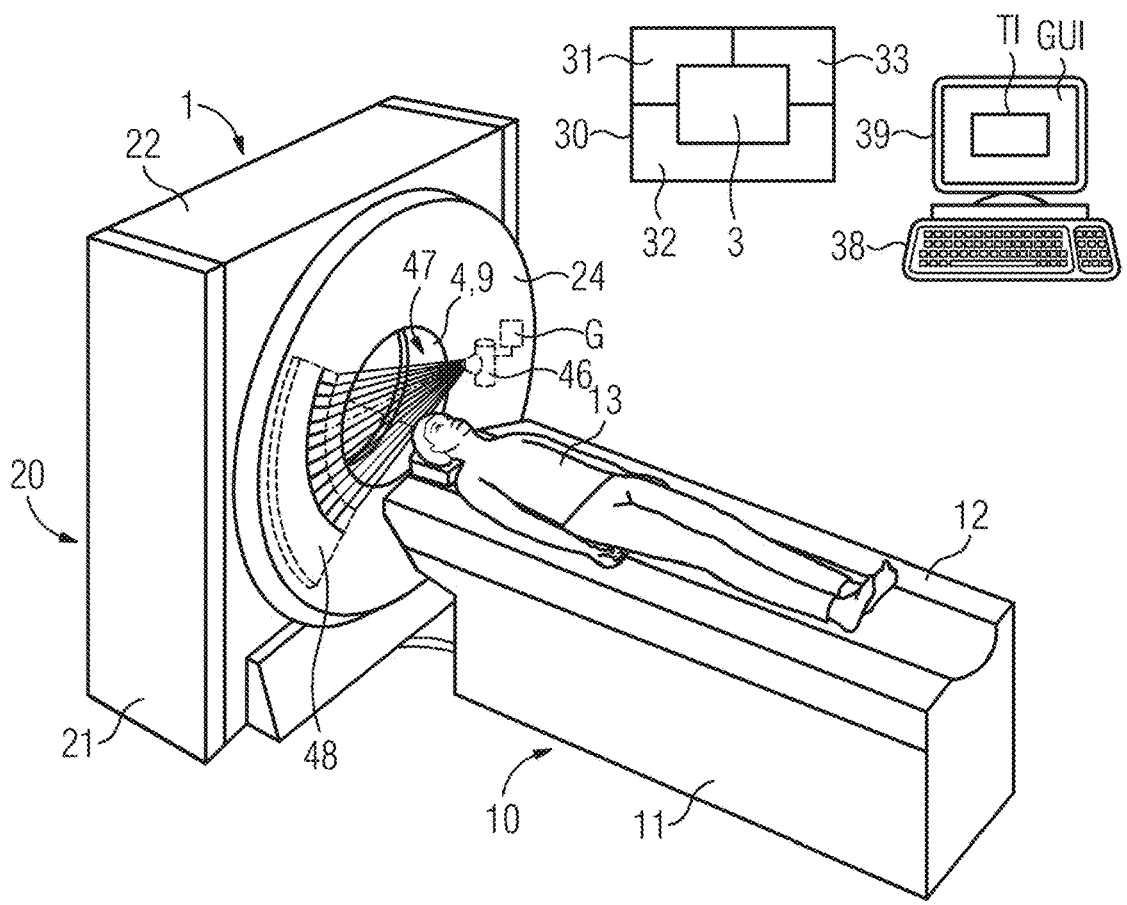
FIG. 4 shows a medical imaging device having an X-ray tube and a load calculator.

FIG. 4 shows a medical imaging device 1 having an X-ray tube 46 and a load calculator 3 as an example of a computer tomography device. The medical imaging device 1 has a gantry 20, a patient bed 10 and a data processing system 30. The gantry 20 has a carrier frame 21, a tilting frame 22, a rotating frame 24 and the tunnel-shaped opening 9. The rotating frame 24 has the X-ray tube 46 for generating the X-rays 47 and the X-ray detector 48 for detecting the X-rays 47.

The patient bed 10 has a bed base 11 and a bed board 12 that is mounted so that it can be displaced relative to the bed base 11 in a longitudinal direction of the bed board 12 so that the patient 13 that is lying on the bed board 12 can be introduced into the tunnel-shaped opening 9 so that an interaction of a region of the patient that is to be investigated with the X-rays 47 can take place in the image data acquisition region 4 that is located in the tunnel-shaped opening 9.

The data processing system 30 has a processor 31, a storage unit 33 and a data transfer interface 32 that together form the load calculator 3. The data processing system 30 can be designed for example in the form of a computer. The medical imaging device 1 moreover has an input unit 38 and an output unit 39 in the form of a screen. The input unit 38 and the output unit 39 form a graphic user interface GUI and for example the temperature information TI can be displayed in said graphic user interface and/or for example a user input can be input into said graphic user interface so as to control the medical device, in particular the load calculator 3.

Figure 5:
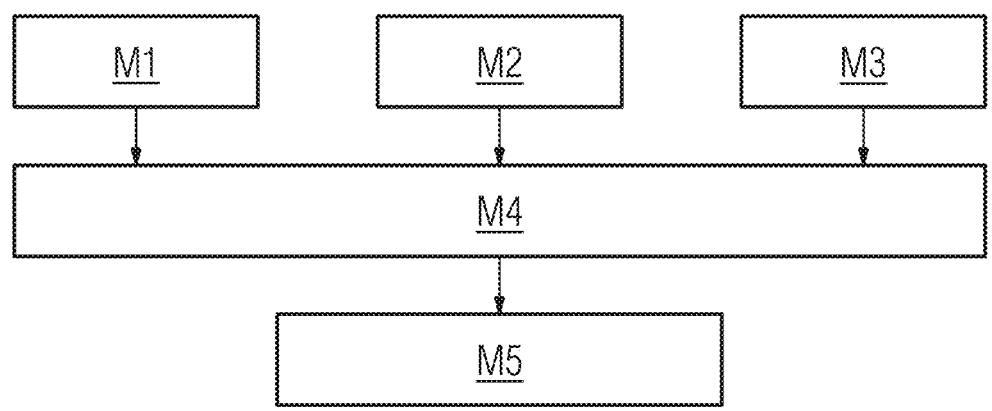
FIG. 5 shows a flow chart of a method for providing temperature information.

FIG. 5 shows a flow chart of a method for providing temperature information TI that relates to an inverter assembly NG of a high voltage generator G for an X-ray tube 46 of a medical imaging device 1, wherein the inverter assembly NG has an inverter N and a cooling body K, the method comprising:
receiving M1 power loss data that relates to the inverter N, receiving M2 a set of thermodynamic coefficients that relates to a heating of the inverter N, which is caused by power loss, a conduction of heat from the inverter N to the cooling body K and a transfer of heat from the cooling body K to a cooling fluid F,
receiving M3 cooling fluid temperature data that relates to the cooling fluid F,
calculating M4 the temperature information TI based on the power loss data, the set of thermodynamic coefficients and the cooling fluid temperature data,
providing M5 the temperature information TI.

Figure 6:
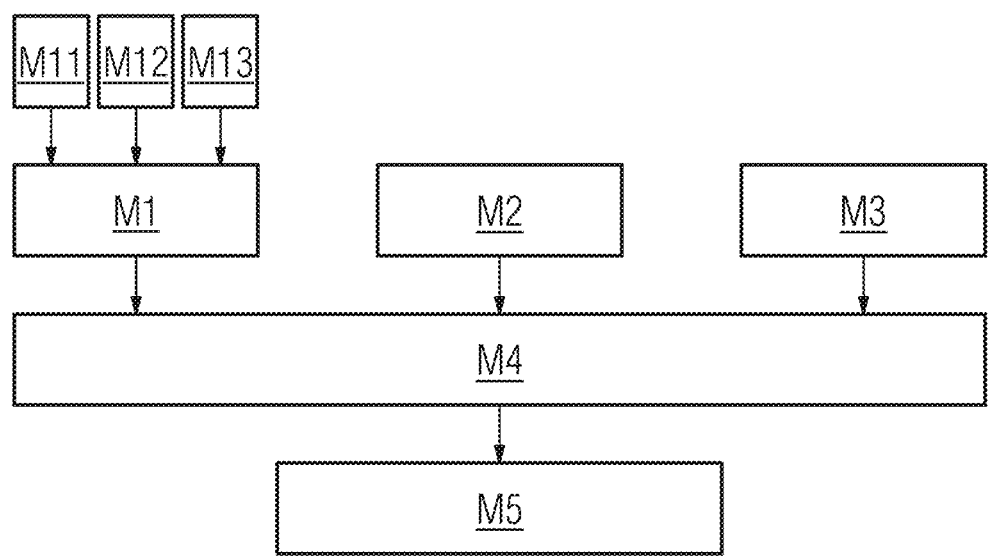
FIG. 6 shows a flow chart of a method for providing temperature information.

FIG. 6 illustrates a flow chart of a method for providing temperature information TI, moreover comprising:
receiving M11 tube current data that relates to a tube current for the X-ray tube 46,
receiving M12 tube voltage data that relates to a tube voltage for the X-ray tube 46,
receiving M13 intermediate circuit direct current voltage data that relates to an intermediate circuit direct current voltage of the inverter N,
wherein the power loss data is calculated based on the tube current data, the tube voltage data and the intermediate circuit direct current data.

Figure 7:
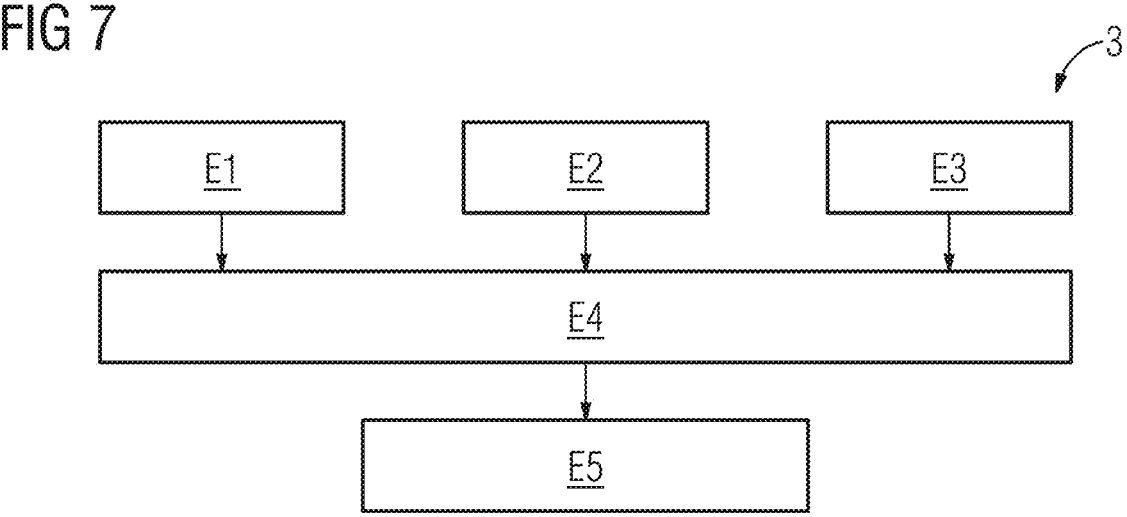
FIG. 7 shows a load calculator for providing temperature information.

FIG. 7 shows a load calculator 3 for providing temperature information TI that relates to an inverter assembly NG of a high voltage generator G for an X-ray tube 46 of a medical imaging device 1, wherein the inverter assembly NG has an inverter N and a cooling body K, the load calculator 3 having:
a power loss data receiving unit E1 for receiving M1 power loss data that relates to the inverter N,
a coefficient receiving unit E2 for receiving M2 a set of thermodynamic coefficients that relates to a heating of the inverter N, which is caused by power loss, a conduction of heat from the inverter N to the cooling body K and a transfer of heat from the cooling body K to a cooling fluid F,
a cooling fluid temperature data receiving unit E3 for receiving M3 cooling fluid temperature data that relates to the cooling fluid F,
a computing unit E4 for calculating M4 the temperature information TI based on the power loss data, the set of thermodynamic coefficients and the cooling fluid temperature data,
a providing unit E5 for providing M5 the temperature information TI.

Figure 8:
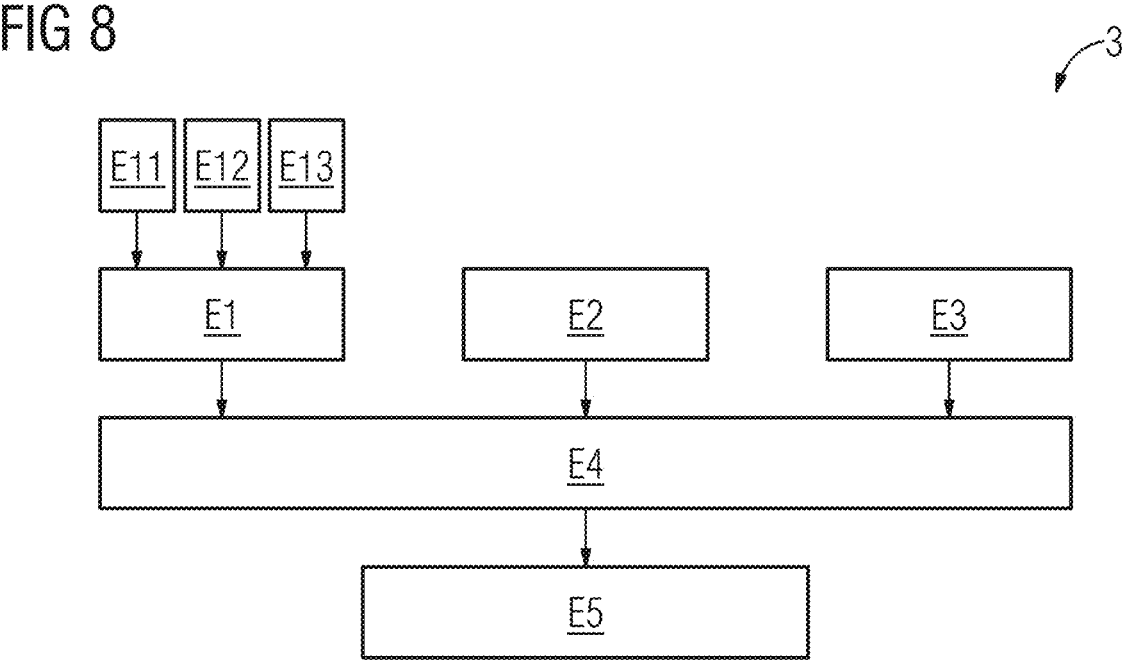
FIG. 8 shows a load calculator for providing temperature information.

FIG. 8 illustrates the load calculator 3, moreover having:
a tube current data receiving unit E1*l* for receiving M11 tube current data that relates to a tube current for the X-ray tube 46,
a tube voltage data receiving unit E12 for receiving M12 tube voltage data that relates to a tube voltage for the X-ray tube 46,
an intermediate circuit direct current voltage data receiving unit E13 for receiving M13 intermediate circuit direct current voltage data that relates to an intermediate circuit direct current voltage of the inverter N,
wherein the power loss data is calculated based on the tube current data, the tube voltage data and the intermediate circuit direct current voltage data.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A method for providing temperature information that relates to an inverter assembly of a high voltage generator for an X-ray tube of a medical imaging device, the inverter assembly having an inverter and a cooling body, the method comprising:
receiving power loss data that relates to the inverter;
receiving a set of thermodynamic coefficients that relates to a heating of the inverter, a conduction of heat from the inverter to the cooling body, and a transfer of heat from the cooling body to a cooling fluid, the heating of the inverter being caused by power loss;
receiving cooling fluid temperature data that relates to the cooling fluid;
calculating the temperature information based on the power loss data, the set of thermodynamic coefficients and the cooling fluid temperature data, the calculating the temperature information being based on
a thermodynamic model of the cooling body, wherein the cooling body includes a first region and a second region, wherein the set of thermodynamic coefficients relates to the conduction of heat from the inverter to the cooling body and the transfer of heat from the cooling body to the cooling fluid in that the set of thermodynamic coefficients relates to a conduction of heat from the inverter to the first region of the cooling body, a conduction of heat from the first region of the cooling body to the second region of the cooling body, and a transfer of heat from the second region of the cooling body to the cooling fluid,
calculating a parameter change based on the temperature information, the parameter change relating to at least one of a tube current, a tube voltage, an intermediate circuit direct current voltage, or a scan duration;
changing the at least one of the tube current, the tube voltage, the intermediate circuit direct current voltage, or the scan duration based on a cooling pause of the medical imaging device being unable to prevent an overheating of the medical imaging device; and
providing the temperature information and the parameter change.

2. The method as claimed in claim 1, further comprising:
receiving tube current data that relates to the tube current for the X-ray tube;
receiving tube voltage data that relates to the tube voltage for the X-ray tube;
receiving intermediate circuit direct current voltage data that relates to the intermediate circuit direct current voltage of the inverter; and
wherein the power loss data is calculated based on the tube current data, the tube voltage data and the intermediate circuit direct current voltage data.

3. The method as claimed in claim 2,
wherein the inverter includes a first half bridge and a second half bridge,
wherein the power loss data includes first power loss data that relates to the first half bridge and second power loss data that relates to the second half bridge,
wherein the set of thermodynamic coefficients includes a first coefficient that relates to a heating of the first half bridge that is based on power loss, and
wherein the set of thermodynamic coefficients includes a second coefficient that relates to a heating of the second half bridge that is based on power loss.

4. The method as claimed in claim 1, wherein the set of thermodynamic coefficients is based on at least one of simulations or measurements.

5. The method as claimed in claim 1,
wherein the inverter includes a first half bridge and a second half bridge,
wherein the power loss data includes first power loss data that relates to the first half bridge and second power loss data that relates to the second half bridge,
wherein the set of thermodynamic coefficients includes a first coefficient that relates to a heating of the first half bridge that is based on power loss, and
wherein the set of thermodynamic coefficients includes a second coefficient that relates to a heating of the second half bridge that is based on power loss.

6. The method as claimed in claim 1,
wherein the calculating of the temperature information is based on the solving of a differential equation system,
wherein a coefficient matrix for a matrix representation of the differential equation system is determined based on the set of thermodynamic coefficients,
wherein an inhomogeneities vector for the matrix representation of the differential equation system is determined based on the set of thermodynamic coefficients, the power loss data, and the cooling fluid temperature data, and
wherein the differential equation system is solved based on a matrix operation.

7. The method as claimed in claim 1,
wherein the set of thermodynamic coefficients includes a coefficient that relates to a temperature difference between a semiconductor junction of the inverter and a housing of the inverter that surrounds the semiconductor junction, upon a power loss of the semiconductor junction of the inverter, and
wherein the temperature information relates to a temperature at the semiconductor junction of the inverter.

8. The method as claimed in claim 1,
wherein the calculating of the temperature information includes a temporal localization of a temperature maximum,
wherein a calculation of a temporal temperature curve is adapted depending on the temporal localization of the temperature maximum, and
wherein the temperature information is calculated based on the temporal temperature curve.

9. The method as claimed in claim 1, further comprising:
receiving threshold value data, wherein
the temperature information is calculated based on the threshold value data and at least one threshold value comparison.

10. The method as claimed in claim 1, further comprising:
calculating time information based on the temperature information, the time information relating to a cooling pause for the high voltage generator; and
providing the time information.

11. A non-transitory computer program product having a computer program, which is loadable directly into a memory of a data processing system, the computer program having program sections to implement the method as claimed in claim 1 when the program sections are executed by the data processing system.

12. A non-transitory computer-readable storage medium storing executable instructions that, when executed by a data processing system, cause the data processing system to implement the method as claimed in claim 1.

13. A load calculator for providing temperature information that relates to an inverter assembly of a high voltage generator for an X-ray tube of a medical imaging device, the inverter assembly having an inverter and a cooling body, and the load calculator comprising:
   a power loss data receiving unit configured to receive power loss data that relates to the inverter;
   a coefficient receiving unit configured to receive a set of thermodynamic coefficients that relates to a heating of the inverter, a conduction of heat from the inverter to the cooling body, and a transfer of heat from the cooling body to a cooling fluid, the heating of the inverter being caused by power loss;
   a cooling fluid temperature data receiving unit configured to receive cooling fluid temperature data that relates to the cooling fluid;
   a computing unit configured to
   calculate the temperature information based on the power loss data, the set of thermodynamic coefficients, and the cooling fluid temperature data, the calculation of the temperature information being based on
   a thermodynamic model of the cooling body, wherein the cooling body includes a first region and a second region, and wherein the set of thermodynamic coefficients relates to the conduction of heat from the inverter to the cooling body and the transfer of heat from the cooling body to the cooling fluid in that the set of thermodynamic coefficients relates to a conduction of heat from the inverter to the first region of the cooling body, a conduction of heat from the first region of the cooling body to the second region of the cooling body, and a transfer of heat from the second region of the cooling body to the cooling fluid, and
   calculate a parameter change based on the temperature information, the parameter change relating to at least one of a tube current, a tube voltage, an intermediate circuit direct current voltage, or a scan duration;
   a parameter changing unit configured to change the at least one of the tube current, the tube voltage, the intermediate circuit direct current voltage, or the scan duration based on a cooling pause of the medical imaging device being unable to prevent an overheating of the medical imaging device; and
   a providing unit configured to provide the temperature information and the parameter change.

14. A medical imaging device comprising:
   an X-ray tube and a load calculator as claimed in claim 13.

15. The medical imaging device as claimed in claim 14, wherein the medical imaging device is an X-ray device, a C-arm X-ray device, or a computer tomography device.

16. A load calculator for providing temperature information that relates to an inverter assembly of a high voltage generator for an X-ray tube of a medical imaging device, the inverter assembly having an inverter and a cooling body, and the load calculator comprising:
   one or more processors; and
   a memory storing computer-executable instructions that, when executed by the one or more processors, cause the load calculator to
   receive power loss data that relates to the inverter,
   receive a set of thermodynamic coefficients that relates to a heating of the inverter, a conduction of heat from the inverter to the cooling body, and a transfer of heat from the cooling body to a cooling fluid, the heating of the inverter being caused by power loss,
   receive cooling fluid temperature data that relates to the cooling fluid,
   calculate the temperature information based on the power loss data, the set of thermodynamic coefficients, and the cooling fluid temperature data, the calculation of the temperature information being based on
   a thermodynamic model of the cooling body, wherein the cooling body includes a first region and a second region, and wherein the set of thermodynamic coefficients relates to the conduction of heat from the inverter to the cooling body and the transfer of heat from the cooling body to the cooling fluid in that the set of thermodynamic coefficients relates to a conduction of heat from the inverter to the first region of the cooling body, a conduction of heat from the first region of the cooling body to the second region of the cooling body, and a transfer of heat from the second region of the cooling body to the cooling fluid,
   calculate a parameter change based on the temperature information, the parameter change relating to at least one of a tube current, a tube voltage, an intermediate circuit direct current voltage, or a scan duration,
   change the at least one of the tube current, the tube voltage, the intermediate circuit direct current voltage, or the scan duration based on a cooling pause of the medical imaging device being unable to prevent an overheating of the medical imaging device, and
   provide the temperature information and the parameter change.

* * * * *